United States Patent
Lombardo et al.

[19]

[11] Patent Number: 6,019,780
[45] Date of Patent: Feb. 1, 2000

[54] DUAL PIN AND GROOVE PIVOT FOR MICRO-INSTRUMENT

[75] Inventors: Giuseppe Lombardo, Bridgewater; Francis J. DiFrancesco, Foxboro; Brian W. Gilman, Halifax; Roger M. Burke, Weston, all of Mass.

[73] Assignee: TNCO, Inc., Whitman, Mass.

[21] Appl. No.: 08/794,213

[22] Filed: Jan. 30, 1997

Related U.S. Application Data

[60] Provisional application No. 60/034,422, Dec. 17, 1996.

[51] Int. Cl.⁷ .................................................. A61B 17/32
[52] U.S. Cl. ......................... 606/207; 606/174; 600/564
[58] Field of Search ................................ 606/51, 52, 174, 606/205–211; 128/750–755; 600/564

[56] References Cited

U.S. PATENT DOCUMENTS

| | | |
|---|---|---|
| 4,712,545 | 12/1987 | Honkanen . |
| 5,395,375 | 3/1995 | Turkel et al. .......................... 606/174 |
| 5,431,674 | 7/1995 | Basile et al. .......................... 606/174 |
| 5,649,947 | 7/1997 | Auerbach et al. ..................... 606/174 |

*Primary Examiner*—Michael Buiz
*Assistant Examiner*—William Lewis
*Attorney, Agent, or Firm*—Jerry Cohen; Stephen Y. Chow; Harvey Kaye

[57] ABSTRACT

A miniature articulating tip for an endoscopic instrument comprising a jaw with a curved slot through which two pivot lugs pass and are anchored in or integral to a fixed outer tip. The two pivot lugs guide the jaw over a path defined by the curved slot and provide stops at the ends of the curve.

67 Claims, 8 Drawing Sheets

DUAL PIN AND GROOVE PIVOT FOR MICRO-INSTRUMENT

Applicants claim priority based on the provisional application No. 60/03440 filed on Dec. 17, 1996, for "DUAL PIN/ARCUATE GROOVE PIVOT."

BACKGROUND OF THE INVENTION

The field of the invention is that of micro-instrumentation, that is, articulating, hand-held, instruments used in micro-surgery, electronic micro-assembly and like applications, for grasping, cutting, punching out, probing and the like.

The invention is particularly advantageous for endoscopic, or minimally invasive, surgery, but is also advantageous in other applications for micro-instrumentation.

Prior art devices are disclosed in U.S. Pat. No. 5,152,790 to Honkanen et al. and U.S. Pat. No. 5,219,357 to Honkanen et al. These patents disclose endoscopic instruments such as shown in FIG. 1A, using effector tips using one or two jaws, for example, jaw 5 in FIG. 1, rotatably mounted on a pivot 6 mounted on a fixed outer tip 7, rotated by an actuating link 3 driven reciprocally by a drive shaft 2, the entire structure being supported by an extension shaft 1 from a handle assembly with a fixed portion 8 and a movable portion 9 linked to and from which the drive shaft 2 is manipulated. A feature of the inventions in the patents is the employment at jaw 5 of a recess 4 off the pivot center 6 to accommodate and absorb force from the distal end of an actuating link 3 connected to jaw 5 by retaining pin 41. This approach improved over traditional scissor-type linkages by minimizing the width of the structure that pushes the jaw closed around the pivot and by minimizing the shear force on a retaining pin 41 or its counterpart in scissor-type linkages.

Although this prior art device has advantages in strength and form factor over the traditional endoscopic instrument, it has limitation in the mechanical advantage achievable in a limited area. The single pivot and retainer pin placement must remain within the envelope of the outer tip at the risk of exposure to tissue which might jam or break the components. Both the limited joint strength and mechanical advantage of the single pivot design limit how small the distal tip can be made and still remain functional and safe.

SUMMARY OF THE INVENTION

It is a particular objective of the present invention to provide an endoscopic instrument effector tip that achieves superior mechanical advantage in a limited area with superior structural reliability.

It is another objective to provide an endoscopic instrument effector tip that can transform drive shaft motion into complex motions including lateral forces for shearing.

The present invention comprises the use of a jaw with a curved slot through which two pivot lugs pass and are anchored in or integral to a fixed outer tip. The two pivot lugs guide the jaw over a path defined by the curved slot and provide stops at the ends of the curve. A simple arc with parallel pivot lugs allows a motion of the jaw over a rotational center of the arc which might be placed (virtually) well beyond the envelope of the inner tip. This supplies mechanical advantage in shearing force as the jaw is pushed forward over a narrower arc with the same work. By making the curve more complex or by biasing the pivot lugs, or both, complex motions of the jaw can be effected from the linear pushing of the drive shaft.

The advantages, in addition to meeting the objectives of the invention, can be seen in detailed the description below.

DETAILED DESCRIPTION

Figure 2:
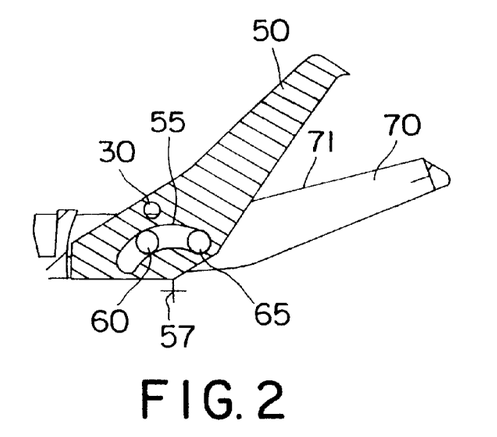
FIG. 2 is a cut-away side view of a preferred embodiment of the present invention with the jaw open.
Figure 5:
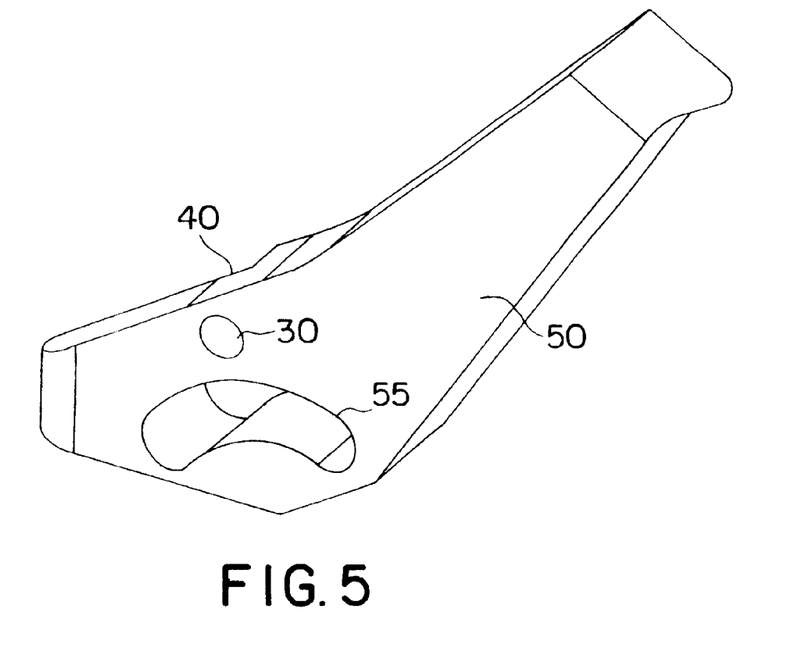
FIG. 5 is an isometric view of the jaw of a preferred embodiment of the present invention.
Figure 6:
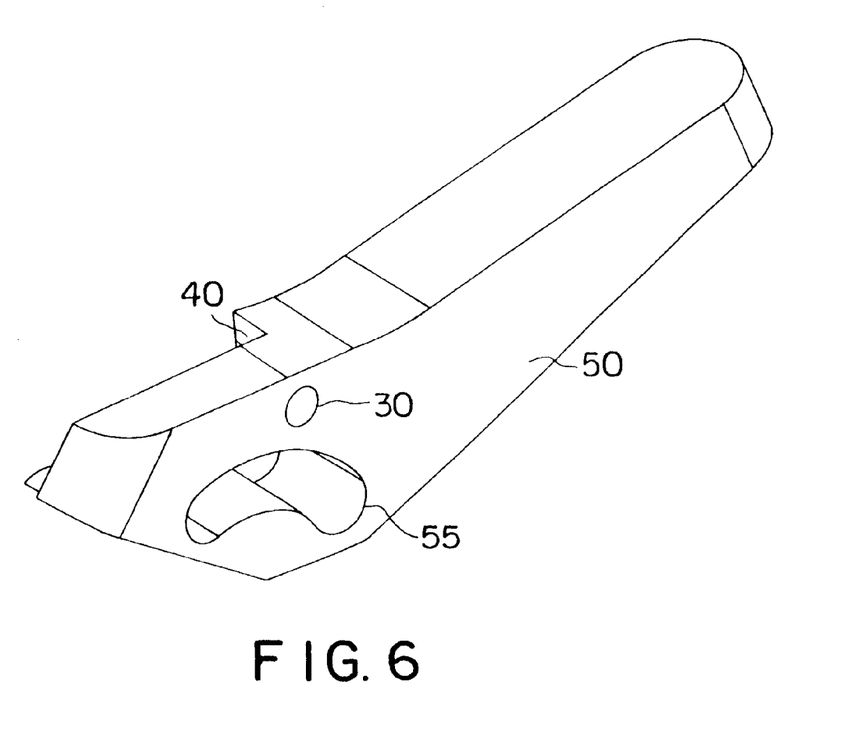
FIG. 6 is an isometric view of the jaw of a preferred embodiment of the present invention from a different angle.

FIG. 2 is a cut-away side view of a preferred embodiment of the present invention with the inner tip or jaw 50 open. This jaw 50 is shown in isometric views in FIGS. 5 and 6, with the curved slot 55, and, in a preferred mode, with recess 40 and retaining pin hole 30 to receive a distal-pushing actuator link as shown in U.S. Pat. No. 5,152,790. In FIG. 2, the actuator link is not shown, but only the assembly of the inner tip or jaw 50, outer tip 70 attached to extension shaft 10 and the back pivot lug 60 and front pivot lug 65, mounted in extension shaft 10 and outer tip 70 and passing through slot 55. The center of curvature of the arcuate slot 55 is also the center of rotation 57, which is outside the envelope of the outer tip. The front of the slot 55 provides an opening stop against front pivot lug 65.

Figure 3:
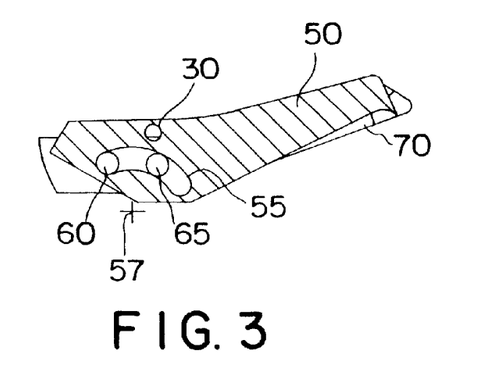
FIG. 3 is a cut-away side view of a preferred embodiment of the present invention with the jaw closed.
Figure 4:
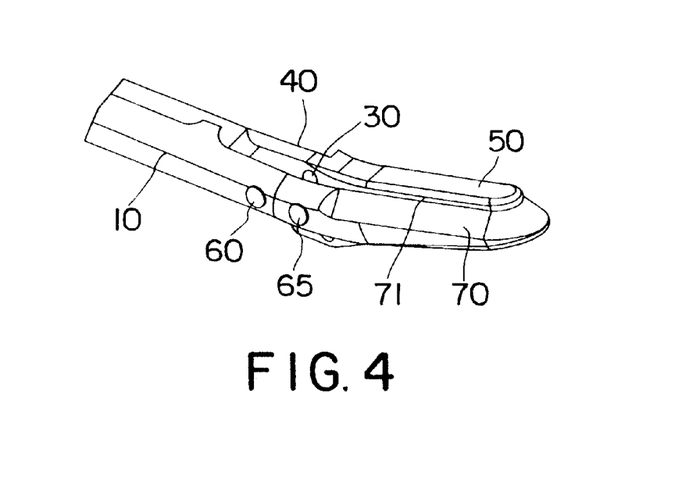
FIG. 4 a perspective view of a preferred embodiment of the present invention with the jaw closed.

FIG. 3 is a cut-away side view with the jaw 50 closed, as shown in perspective view in FIG. 4. Here, the jaw 50 has been pushed forward (by the unshown actuator link) along the track of slot 55 until the back of slot 55 is stopped against back pivot lug 60 as a closing stop. Because the center of rotation 57 is placed beyond where a single pivot would be, but the pushing action applied at recess 40 is still made within the envelope of outer tip 70, there is less angular rotation, but the pushing force may be applied over a greater linear distance, increasing the mechanical advantage. The placement of the outer tip to provide cutting edge 71 off a radius from the center of rotation provides added shearing action relative to that available in the prior art.

In the embodiment shown in FIGS. 2–6, the jaw 50 is formed with slot 55, assembled with the slot portion inside the cavity provided by outer tip 70, and pivot lugs 60 and 65 inserted through one wall of outer tip 70, through slot 55 and through the other wall of outer tip 70, then finished. The two pivot lugs provide greater strength and cavity stability than a single pin design.

Figure 7:
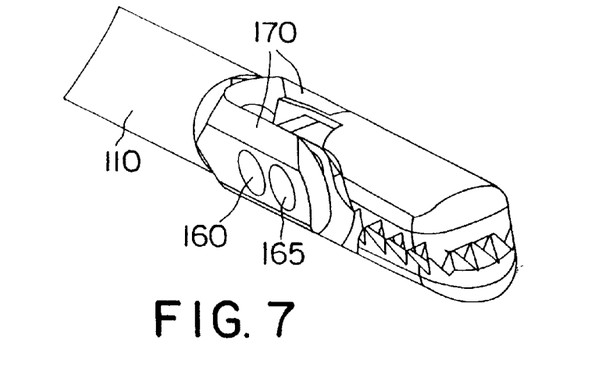
FIG. 7 is an isometric view of a double-action alternate version of the present invention with enclosing walls.
Figure 7A:
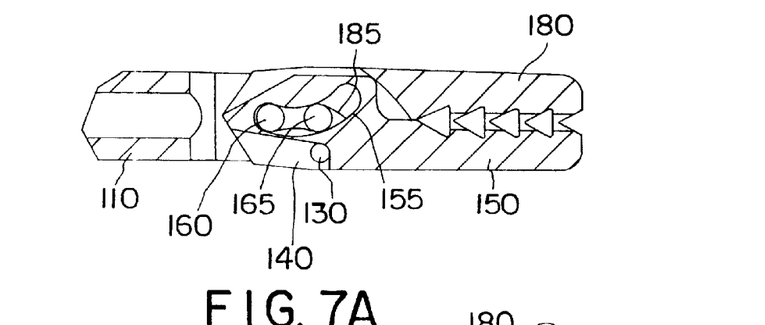
FIG. 7A is a cross-section of the double-action version of FIG. 7 in closed position.
Figure 7B:
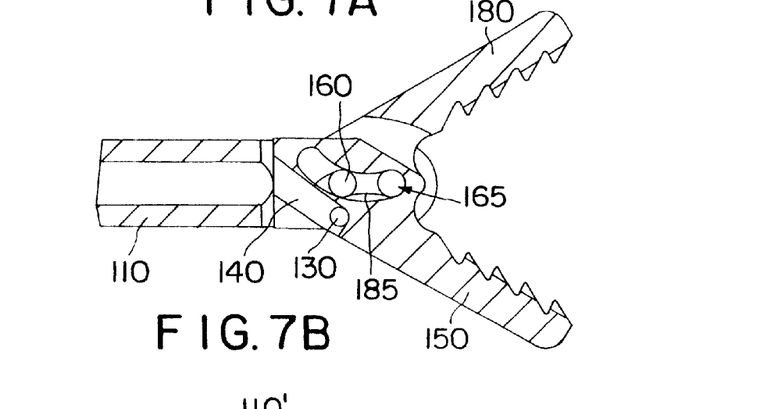
FIG. 7B is a cross-section of the double-action version of FIG. 7 in open position
Figure 8:
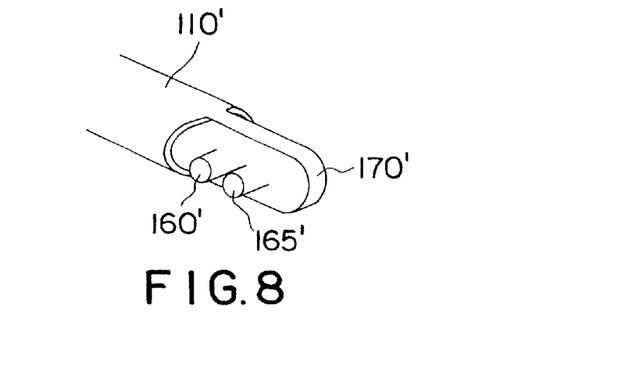
FIG. 8 is an isometric view of the center wall of a center-wall mounted version of the invention.

It can be seen that there are many variations possible, using the same back end, extension shaft, drive shaft and actuator link used the prior art "distal-pushing" configurations discussed in the background or with traditional scissor-style linkages. Indeed the invention may be used for pull to close (push to open) configurations by inverting the arc or the point of pushing by the drive linkage. Nor is the invention limited to single action jaw styles. It may be adapted to dual action designs which incorporate two movable jaws with a fixed structure, a central wall or enclosing walls for, respectively, two pairs or one pair of pivot lugs. FIG. 7 shows a dual action version of the invention using a pair of lugs 160 and 165 fitted in an enclosing wall extension of extension shaft 110. Although the drive shaft and actuating link is not shown, FIGS. 7A and 7B show the embodiment respectively in the closed and open positions. An actuating element would fit into the slot 140 and be connected to jaw 150 at pin hole 130 in this push-to-close configuration. Arcuate slot 155 is shown for jaw 150 and arcuate slot 185 is shown for opposing jaw 180. FIG. 8 shows a version with a central wall 170' supporting a pair of lugs 160' and 165' on which a jaw (not shown) may be fitted, and which may have a second set of lugs (not shown) on the opposite face of the central wall to support a second jaw.

Figure 9:
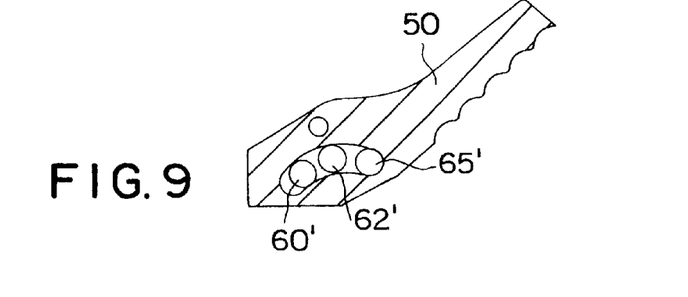
FIG. 9 is a cross-section of a jaw with three pins in the arcuate slot, in an alternative version of the invention.
Figure 10:
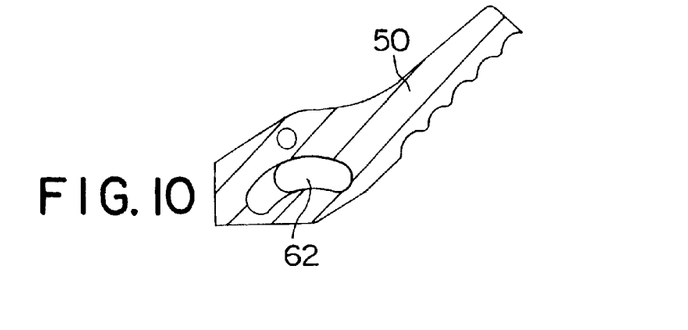
FIG. 10 is a cross-section of a jaw with an arcuate lug in the arcuate slot, in an alternative version of the invention.

The lugs themselves may be integrally machined with the fixed structure (for example, outer tip, or the center wall, as shown in FIG. 8) to provide additional strength and stability. Where the slot is a simple arc, additional pivot lugs, for example, lug 62' in FIG. 9, may be added between the back and front pivot lugs or may be integrated into one continuous arcuate piece 62 (FIG. 10) to provide additional strength.

Figure 1:
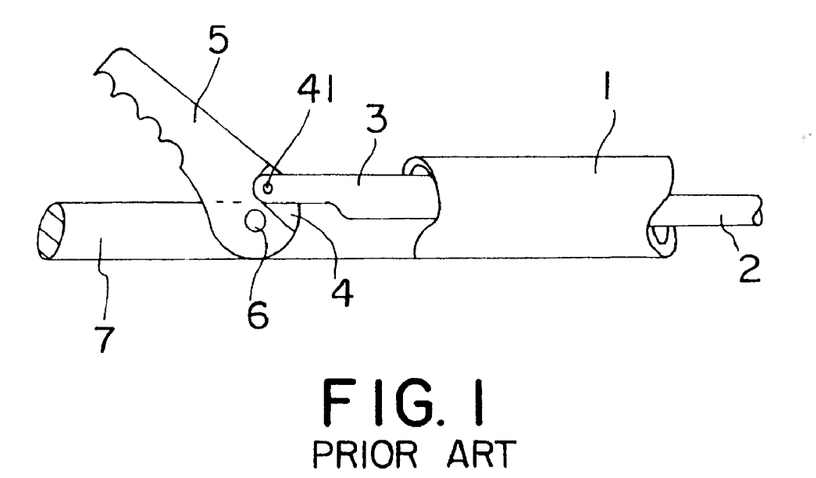
FIG. 1 is a cut-away side view of a prior art effector tip.
Figure 1A:
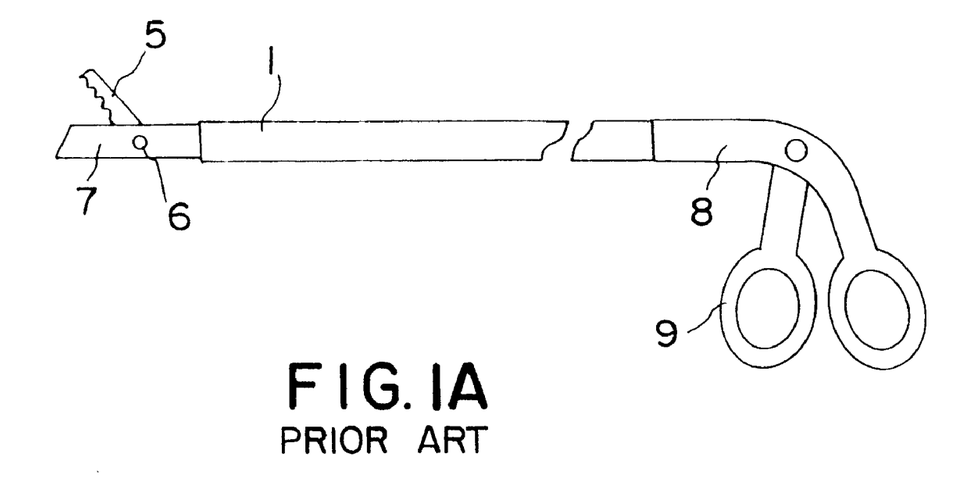
FIG. 1A depicts the general configuration of a pistol-handle style endoscopic instrument employing a prior art effector tip.
Figure 11:
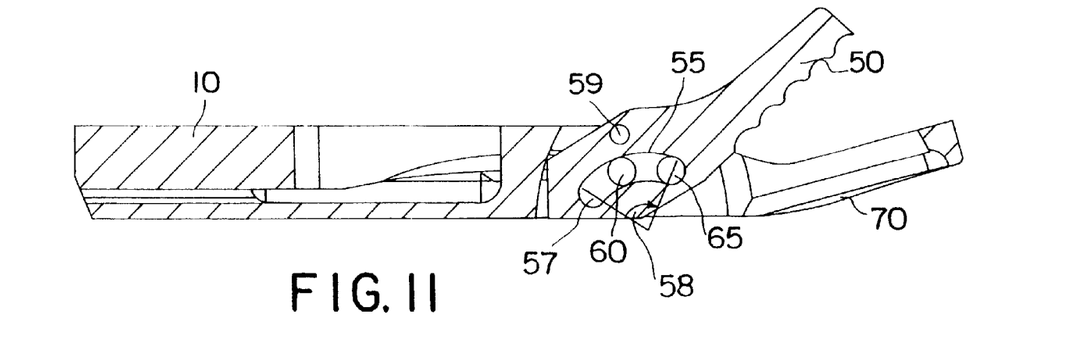
FIG. 11 is a cross-section of the invention showing parameters that may be varied.

The type and extent of motion can be varied greatly using the same back end (extension shaft 1, drive shaft 2, linkage 3, fixed handle 8 and movable handle 9 in FIG. 1). For example, the radius of curvature 57 (FIG. 11) of the slot may be varied, the angular range of rotation 58 (FIG. 11) may be varied by varying the length of the slot and the distance between pivot centers, and the torque may be varied by varying the point of application of actuation force 59 (FIG. 11).

Figure 12:
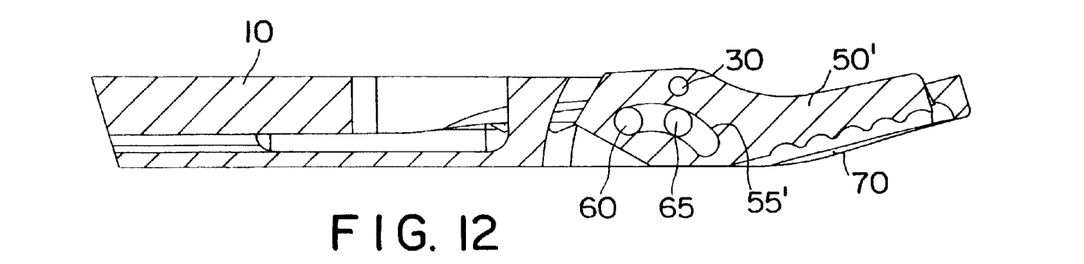
FIG. 12 is a cross-section of the invention with an arcuate slot of different radii of curvature, in an alternative version of the invention.
Figure 13A:
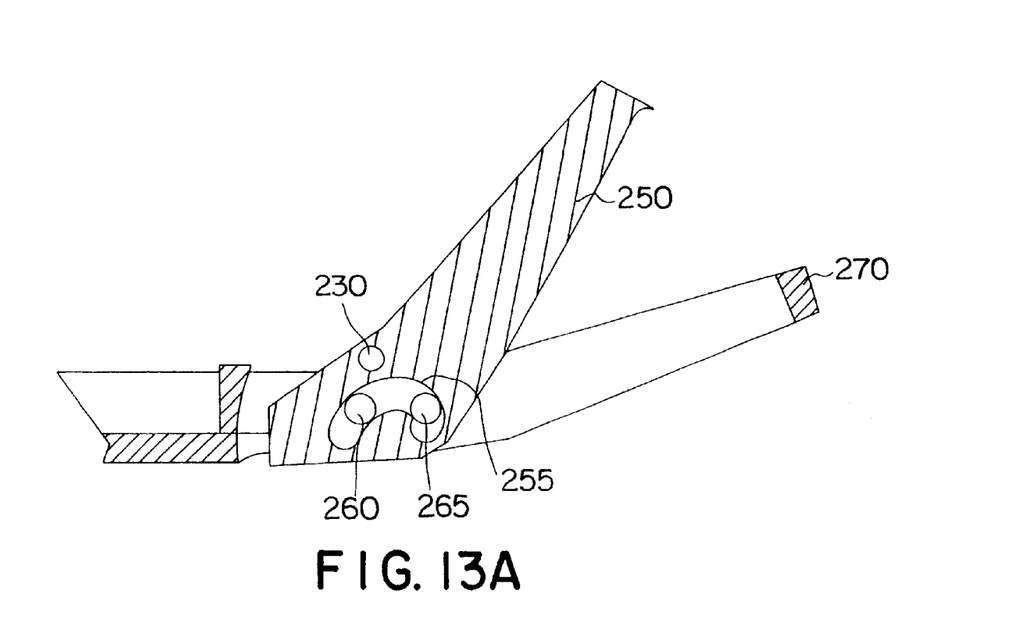
FIG. 13A and 13B are respectively cross-sections of the invention with an involute curve slot in open and closed positions, in an alternative version of the invention.
Figure 13B:
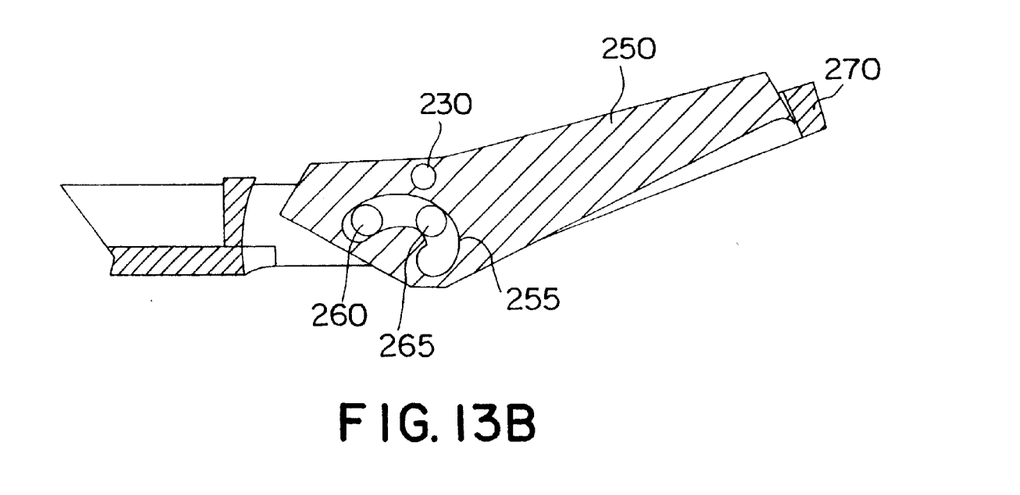

The shape of the slot is not limited to a simple arc. Other curves, including a variable radius curve 55' (FIG. 12) or an involute curve 255 (FIGS. 13A and 13B), may be used to provide specific motions or variations in the transmission of force. The slot may be a groove rather than a through-slot, for example, slot 455 in FIGS. 15A–15C.

Figure 14:
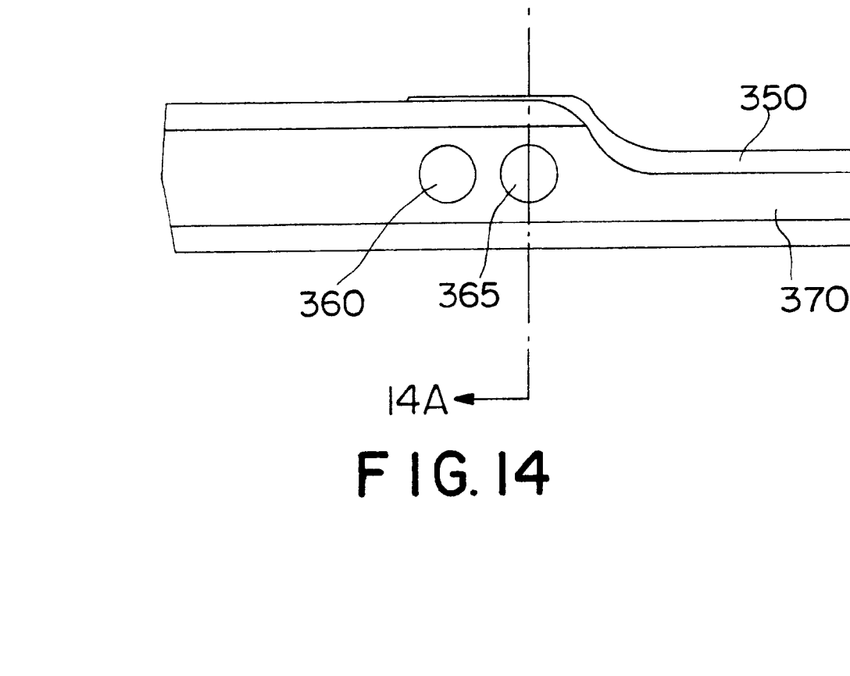
FIG. 14 is a side view of an alternative version of the invention showing a skewed cross pin.
Figure 14A:
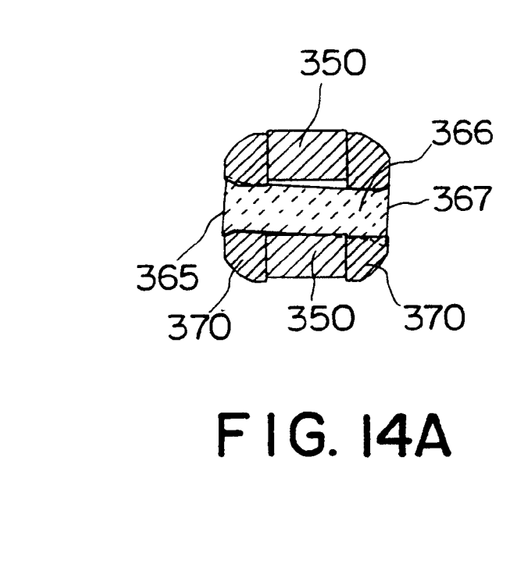
FIG. 14A is a cross-section of the alternative version shown in FIG. 14.

The cross pins (pivot lugs) need not be perpendicular to the wall(s), but may be skewed to provide normal force in shearing action between jaws, such as in scissors applications. FIGS. 14 and 14A show such a skewed cross pin configuration, where one end 365 of pin or lug 366 is higher in FIG. 14A than the other end 367.

Figures 15, 15A, 15B:
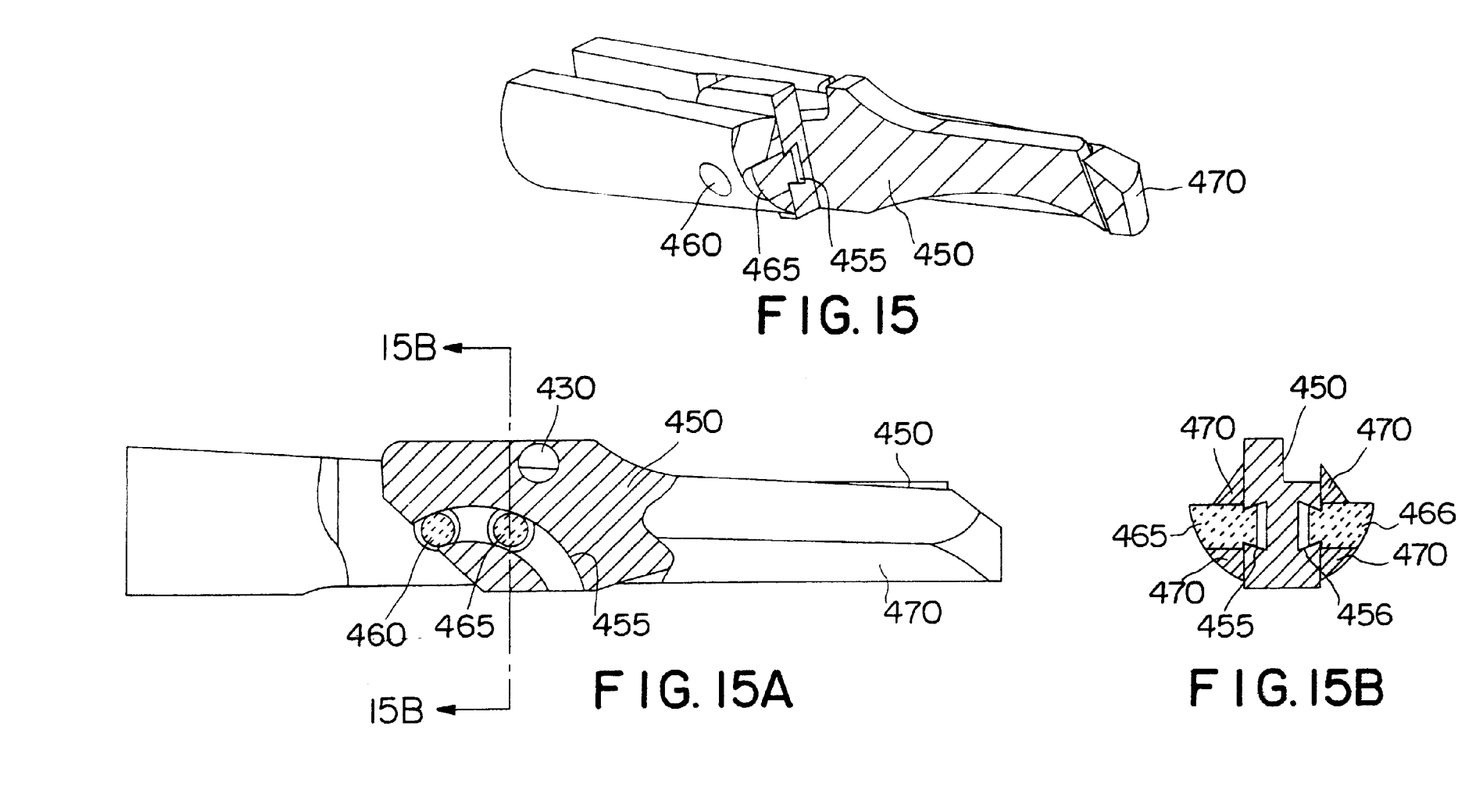
FIG. 15 is a cut-away view of an alternative version of the invention showing multiple short pins in groove-type slots.
FIG. 15A is a cut-away side view of the alternative version shown in FIG. 15.
FIG. 15B is a cross-section of the alternative version shown in FIG. 15A.

As shown in FIGS. 15A–15C, the cross pins could be replaced by multiple shorter pins 460, 465 and 466 (counterpart to 460 not shown), which would extend from an outer tip cavity walls 470 into arcuate grooves 455 and 456 partially formed into both sides of the movable jaw 450. The pins 460, 465 and 466 may be dovetailed to capture the movable jaw 450 and stabilize the cavity under high loads. In this multiple pin variation, the arcuate groove center positions and radii may differ from ones side of the movable jaw to the other to provide skewed articulation, similarly to the variation shown in FIGS. 14 and 14A.

As can be seen from the above disclosure, the variations on implementation of the multiple lug/pin and arcuate groove configuration may be combined to achieve different results.

What is claimed is:

1. A miniature articulating tip assembly comprising:
    (a) a tip support structure having proximal and distal ends;
    (b) a back pivot lug extending substantially perpendicularly from a lateral portion of said tip support structure,
    (c) a front pivot lug extending substantially perpendicularly from said lateral portion of said tip support structure at a position distal to said back pivot lug; and
    (d) a jar movable relative to said tip support structure, said jaw adapted with a groove for engaging both said back pivot and front pivot lugs, and said jaw engage said lugs with said engagement of said groove with said lugs defining a path of movement of said jaw relative to said tip support structure.

2. The apparatus of claim 1 wherein said groove is cut through said jaw.

3. The apparatus of claim 1 wherein said groove is arcuate.

4. The apparatus of claim 2 wherein said back pivot lug and said front pivot lug are materially integrated with an arcuate cross section conforming to said groove.

5. The apparatus of claim 1 wherein the groove is an involute curve.

6. The apparatus of claim 1 wherein said front and back pivot lugs are fabricated as a single piece with said lateral portion of said tip support structure.

7. A miniature articulating tip assembly comprising:
    (a) a tip support structure having proximal and distal ends and sidewalls defining a cavity;
    (b) a back pivot lug connecting said side walls across said cavity;
    (c) a front pivot lug connecting said side walls across said cavity at a position distal to said back pivot lug; and
    (d) a jaw movable relative to said tip support structure, said jaw adapted with a slot for seating said back pivot and front pivot lugs, and said jaw engaging said lug with said seating of said lugs in said slot defining a path of movement of said jaw relative to said tip support structure.

8. The apparatus of claim 7 wherein said slot is arcuate.

9. The apparatus of claim 8 wherein said back pivot lug and said front pivot lug are materially integrated with an arcuate cross section conforming to said slot.

10. The apparatus of claim 7 wherein the slot is an involute curve.

11. The apparatus of claim 7 wherein said front and back pivot lugs are fabricated as a single piece with said side walls.

12. The apparatus of claim 7 wherein said side walls are parallel and said front and back pivot lugs are orthogonal to said walls.

13. The apparatus of claim 7 wherein said side walls are parallel and at least one pivot lug connects one side wall at a non-orthogonal angle.

14. A miniature articulating tip assembly comprising:
   (a) a tip support structure having proximal and distal ends and side walls defining a cavity;
   (b) a first back pivot lug extending into, but not across, said cavity, from a first said side wall;
   (c) a first front pivot lug extending into, but not across, said cavity from said first side wall at a position distal to said first back pivot lug;
   (d) a second back pivot lug extending into, but not across, said cavity from the second said side wall;
   (e) a second front pivot lug extending into, but not across, said cavity from said second side wall at a position distal to said second back pivot lug; and
   (f) a jaw movable relative to said tip support structure, said jaw adapted on a first side with a first groove for engaging said first back and front lugs and on a second side with a second groove for engaging said second back and front pivot lugs, and said jaw engaging said lugs with said engagement of said grooves with said lugs defining a path of movement of said jaw relative to said tip support structure.

15. The apparatus of claim 14 wherein said grooves are arcuate.

16. The apparatus of claim 15 wherein at least one set of back and front pivot lugs are materially integrated with an arcuate cross section conforming to their corresponding groove.

17. The apparatus of claim 15 wherein at least one of said grooves is an involute curve.

18. The apparatus of claim 15 wherein said pivot lugs are fabricated as a single piece with the side walls to which they are connected.

19. The apparatus of claim 15 wherein said side walls are parallel and said pivot lugs are orthogonal to said walls.

20. The apparatus of claim 15 wherein said side walls are parallel and at least one pivot lug connects one side wall at a non-orthogonal angle.

21. A miniature articulating tip assembly comprising:
   (a) a tip support structure having proximal and distal ends and side walls defining a cavity;
   (b) a back pivot lug connecting said side walls across said cavity;
   (c) a front pivot lug connecting said side walls across said cavity at a position distal to said back pivot lug;
   (d) a first jaw movable relative to said tip support structure, said jaw adapted with a first slot for seating said back and front pivot lugs, and said jaw engaging said lugs with said seating of said lugs in said slot defining a path of movement of said jaw relative to said tip support structure; and
   (e) a second jaw movable relative to said tip support structure, said jaw adapted with a second slot for seating said back and front pivot lugs, and said jaw engaging said lugs with said seating of said lugs in said slot defining a path of movement of said jaw relative to said tip support structure.

22. The apparatus of claim 21 wherein said first and second jaws are moved proximally and distally in unison.

23. The apparatus of claim 22 wherein said first and second slots are arcuate and adapted to coordinate rotation of said first and second jaws with their unitary proximal and distal movement.

24. The apparatus of claim 21 wherein at least one of said slots is an involute curve.

25. The apparatus of claim 21 wherein said front and back pivot lugs are fabricated as a single piece with said side walls.

26. The apparatus of claim 21 wherein said side walls are parallel and said front and back pivot lugs are orthogonal to said walls.

27. The apparatus of claim 21 wherein said side walls are parallel and at least one pivot lug connects one side wall at a non-orthogonal angle.

28. A miniature articulating tip assembly comprising:
   (a) a tip support structure having proximal and distal ends and side walls defining a cavity;
   (b) a first back pivot lug extending into, but not across, said cavity, from a first said side wall;
   (c) a first front pivot lug extending into, but not across, said cavity from said first side wall at a position distal to said first back pivot lug;
   (d) a second back pivot lug extending into, but not across, said cavity from the second said side wall;
   (e) a second front pivot lug extending into, but not across, said cavity from said second side wall at a position distal to said second back pivot lug;
   (f) a first jaw movable relative to said tip support structure, said jaw adapted with a first groove for engaging said first back and front pivot lugs, and said jaw engaging said lugs with said engagement of said groove with said lugs defining a path of movement of said jaw relative to said tip support structure; and
   (g) a second jaw movable relative to said tip support structure, said jaw adapted with a second groove for engaging said second back and front pivot lugs, and said jaw engaging said lugs with said engagement of said groove with said lugs defining a path of movement of said jaw relative to said tip support structure.

29. The apparatus of claim 28 wherein said first and second jaws are moved proximally and distally in unison.

30. The apparatus of claim 29 wherein said first and second grooves are arcuate and adapted to coordinate rotation of said first and second jaws with their unitary proximal and distal movement.

31. The apparatus of claim 29 wherein at least one set of back and front pivot lugs are materially integrated with an arcuate cross section conforming to their corresponding groove.

32. The apparatus of claim 28 wherein at least one of said grooves is an involute curve.

33. The apparatus of claim 28 wherein said pivot lugs are fabricated as a single piece with the side walls to which they are connected.

34. The apparatus of claim 28 wherein said side walls are parallel and said pivot lugs are orthogonal to said walls.

35. The apparatus of claim 23 wherein said side walls are parallel and at least one pivot lug connects one side wall at a non-orthogonal angle.

36. A miniature articulating tip assembly comprising:
   (a) a tip support structure having proximal and distal ends and providing a wall;

(b) a first back pivot lug extending substantially perpendicularly from a first side of said wall;

(c) a first front pivot lug extending substantially perpendicularly from said first side of said wall at a position distal to said first back pivot lug;

(d) a second back pivot lug extending substantially perpendicularly from the second side of said wall;

(e) a second front pivot lug extending substantially perpendicularly from said second side of said wall at a position distal to said second back pivot lug;

(f) a first jaw movable relative to said tip support structure, said jaw adapted with a first groove for engaging said first back and front pivot lugs, and said jaw engaging said lugs with said engagement of said groove with said lugs defining a path of movement of said jaw relative to said tip support structure; and (g) a second jaw movable relative to said tip support structure, said jaw adapted with a second groove for engaging said second back and front pivot lugs, and said jaw engaging said lugs with said engagement of said groove with said lugs defining a path of movement of said jaw relative to said tip support structure.

37. The apparatus of claim 36 wherein said first and second jaws are moved proximally and distally in unison.

38. The apparatus of claim 37 wherein said first and second grooves are arcuate and adapted to coordinate rotation of said first and second jaws with their unitary proximal and distal movement.

39. The apparatus of claim 38 wherein at least one set of back and front pivot lugs are materially integrated with an arcuate cross section conforming to their corresponding groove.

40. The apparatus of claim 37 wherein at least one of said grooves is an involute curve.

41. The apparatus of claim 37 wherein said pivot lugs are fabricated as a single piece with said wall.

42. The apparatus of claim 37 wherein said sides of said wall are parallel and said pivot lugs are orthogonal to said sides.

43. The apparatus of claim 37 wherein said sides of said wall are parallel and at least one pivot lug connects one said side of said wall at a non-orthogonal angle.

44. A miniature articulating instrument comprising:

(a) a handle assembly;

(b) a drive shaft reciprocally movable proximally and distally from said handle assembly;

(c) a tip support structure connected to said handle assembly;

(d) a back pivot lug extending substantially perpendicularly from a lateral portion of said tip support structure;

(e) a front pivot lug extending substantially perpendicularly from said lateral portion of said tip support structure at a position distal to said back pivot lug; and (f) a jaw connected to said drive shaft and movable relative to said tip support structure, said jaw adapted with a groove for engaging both said back pivot and front pivot lugs, and said jaw engaging said lugs with said engagement of said groove with said lugs defining a path of movement of said jaw relative to said tip support structure.

45. The apparatus of claim 44 wherein said handle assembly comprises (i) a fixed portion connected to said tip support structure and (ii) a movable portion connected to said drive shaft.

46. The apparatus of claim 45 wherein said fixed and movable portions of said handle assembly each comprise a finger loop.

47. The apparatus of claim 44 wherein said jaw is connected to said drive shaft by a link to said drive shaft adapted to transmit force in the distal direction from said drive shaft to said jaw at a distal portion of said link.

48. A miniature articulating instrument comprising:

(a) a handle assembly;

(b) a drive shaft reciprocally movable proximally and distally from said handle assembly;

(c) a tip support structure connected to said handle assembly and having side walls defining a cavity;

(d) a back pivot lug connecting said side walls across said cavity;

(e) a front pivot lug connecting said side walls across said cavity at a position distal to said back pivot lug; and (g) a jaw connected to said drive shaft and movable relative to said tip support structure, said jaw-adapted with a slot for seating said back pivot and front pivot lugs, and said jaw engaging said lugs with said seating of said lugs in said slot defining a path of movement of said jaw relative to said tip support structure.

49. The apparatus of claim 48 wherein said handle assembly comprises (i) a fixed portion connected to said tip support structure and (ii) a movable portion connected to said drive shaft.

50. The apparatus of claim 49 wherein said fixed and movable portions of said handle assembly each comprise a finger loop.

51. The apparatus of claim 50 wherein said jaw is connected to said drive shaft by a link to said drive shaft adapted to transmit force in the distal direction from said drive shaft to said jaw at a distal portion of said link.

52. A miniature articulating instrument comprising:

(a) a handle assembly;

(b) a drive shaft reciprocally movable proximally and distally from said handle assembly;

(c) a tip support structure connected to said handle assembly and having side walls defining a cavity;

(d) a first back pivot lug extending into, but not across, said cavity, from a first said side wall;

(e) a first front pivot lug extending into, but not across, said cavity from said first side wall at a position distal to said first back pivot lug;

(f) a second back pivot lug extending into, but not across, said cavity from the second said side wall;

(g) a second front pivot lug extending into, but not across, said cavity from said second side wall at a position distal to said second back pivot lug; and (h) a jaw connected to said drive shaft and movable relative to said tip support structure, said jaw adapted on a first side with a first groove for engaging said first back and front lugs and on a second side with a second groove for engaging said second back and front pivot lugs, and said jaw engaging said lugs with said engagement of said grooves with said lugs defining a path of movement of said jaw relative to said tip support structure.

53. The apparatus of claim 52 wherein said handle assembly comprises (i) a fixed portion connected to said tip support structure and (ii) a movable portion connected to said drive shaft.

54. The apparatus of claim 53 wherein said fixed and movable portions of said handle assembly each comprise a finger loop.

55. The apparatus of claim 52 wherein said jaw is connected to said drive shaft by a link to said drive shaft adapted to transmit force in the distal direction from said drive shaft to said jaw at a distal portion of said link.

56. A miniature articulating instrument comprising:
   (a) a handle assembly;
   (b) a drive shaft reciprocally movable proximally and distally from said handle assembly;
   (c) a tip support structure connected to said handle assembly and having side walls defining a cavity;
   (d) a back pivot lug connecting said side walls across said cavity;
   (e) a front pivot lug connecting said side walls across said cavity at a position distal to said back pivot lug;
   (f) a first jaw connected to said drive shaft and movable relative to said tip support structure, said jaw adapted with a first slot for seating said back and front pivot lugs, and said jaw engaging said lugs with said seating of said lugs in said slot defining a path of movement of said jaw relative to said tip support structure; and
   (e) a second jaw connected to said drive shaft and movable relative to said tip support structure, said jaw adapted with a second slot for seating said back and front pivot lugs, and said jaw engaging said lugs with said seating of said lugs in said slot defining a path of movement of said jaw relative to said tip support structure.

57. The apparatus of claim 56 wherein said handle assembly comprises (i) a fixed portion connected to said tip support structure and (ii) a movable portion connected to said drive shaft.

58. The apparatus of claim 57 wherein said fixed and movable portions of said handle assembly each comprise a finger loop.

59. The apparatus of claim 56 wherein said jaws are connected to said drive shaft by links to said drive shaft adapted to transmit force in the distal direction from said drive shaft to said jaws at distal portions of said links.

60. A miniature articulating instrument comprising:
   (a) a handle assembly;
   (b) a drive shaft reciprocally movable proximally and distally from said handle assembly;
   (c) a tip support structure connected to said handle assembly separate from said drive shaft, said tip support structure having side walls defining a cavity;
   (d) a first back pivot lug extending into, but not across, said cavity, from a first said side wall;
   (e) a first front pivot lug extending into, but not across, said cavity from said first side wall at a position distal to said first back pivot lug;
   (f) a second back pivot lug extending into, but not across, said cavity from the second said side wall;
   (g) a second front pivot lug extending into, but not across, said cavity from said second side wall at a position distal to said second back pivot lug;
   (h) a first jaw connected to said drive shaft and movable relative to said tip support structure, said jaw adapted with a first groove for engaging said first back and front pivot lugs, and said jaw engage said lugs with said engagement of said groove with said lugs defining a path of movement of said jaw relative to said tip support structure; and
   (i) a second jaw connected to said drive shaft and movable relative to said tip support structure, said jaw adapted with a second groove for engaging said second back and front pivot lugs, and said jaw engaging said lugs with said engagement of said groove with said lugs defining a path of movement of said jaw relative to said tip support structure.

61. The apparatus of claim 60 wherein said handle assembly comprises (i) a fixed portion connected to said tip support structure and (ii) a movable portion connected to said drive shaft.

62. The apparatus of claim 61 wherein said fixed and movable portions of said handle assembly each comprise a finger loop.

63. The apparatus of claim 60 wherein said jaws are connected to said drive shaft by links to said drive shaft adapted to transmit force in the distal direction from said drive shaft to said jaws at distal portions of said links.

64. A miniature articulating instrument comprising:
   (a) a handle assembly;
   (b) a drive shaft reciprocally movable proximally and distally from said handle assembly;
   (c) a tip support structure connected to said handle assembly and providing a wall;
   (d) a first back pivot lug extending substantially perpendicularly from a first side of said wall;
   (e) a first front pivot lug extending substantially perpendicularly from said first side of said wall at a position distal to said first back pivot lug;
   (f) a second back pivot lug extending substantially perpendicularly from the second side of said wall;
   (g) a second front pivot lug extending substantially perpendicularly from said second side of said wall at a position distal to said second back pivot lug;
   (h) a first jaw connected to said drive shaft and movable relative to said tip support structure, said jaw adapted with a first groove for engaging said first back and front pivot lugs, and said jaw engaging said lugs with said engagement of said groove with said lugs defining a path of movement of said jaw relative to said tip support structure; and
   (i) a second jaw connected to said drive shaft and movable relative to said tip support structure, said jaw adapted with a second groove for engaging said second back and front pivot lugs, and said jaw engaging said lugs with said engagement of said groove with said lugs defining a path of movement of said jaw relative to said tip support structure.

65. The apparatus of claim 64 wherein said handle assembly comprises (i) a fixed portion connected to said tip support structure and (ii) a movable portion connected to said drive shaft.

66. The apparatus of claim 65 wherein said fixed and movable portions of said handle assembly each comprise a finger loop.

67. The apparatus of claim 64 wherein said jaws are connected to said drive shaft by links to said drive shaft adapted to transmit force in the distal direction from said drive shaft to said jaws at distal portions of said links.

* * * * *